United States Patent [19]
Palumbo

[11] Patent Number: 5,804,605
[45] Date of Patent: Sep. 8, 1998

[54] ABSORBENT MATERIAL

[75] Inventor: Gianfranco Palumbo, Bad Homburg, Germany

[73] Assignee: The Procter & Gamble Company, Cincinnati, Ohio

[21] Appl. No.: 836,123

[22] PCT Filed: Nov. 13, 1995

[86] PCT No.: PCT/US95/14678

§ 371 Date: May 12, 1997

§ 102(e) Date: May 12, 1997

[87] PCT Pub. No.: WO96/15180

PCT Pub. Date: May 23, 1996

[30] Foreign Application Priority Data

Nov. 10, 1994 [IT] Italy .................................. T094A0889

[51] Int. Cl.$^6$ ........................................................ C08J 5/20
[52] U.S. Cl. ............................................................ 521/28
[58] Field of Search .............................. 521/28; 524/503; 525/57, 58

[56] References Cited

U.S. PATENT DOCUMENTS

| | | | |
|---|---|---|---|
| 3,930,074 | 12/1975 | Drelich | 524/45 |
| 4,548,847 | 10/1985 | Aberson | 524/186 |
| 5,122,577 | 6/1992 | Noda | 525/426 |
| 5,200,036 | 4/1993 | Noda | 162/164.3 |
| 5,274,018 | 12/1993 | Tanaka | 526/166 |
| 5,324,561 | 6/1994 | Rezai | 428/72 |
| 5,384,343 | 1/1995 | Farrar | 523/129 |
| 5,461,085 | 10/1995 | Nagatomo et al. | 521/183 |
| 5,466,731 | 11/1995 | Akers et al. | 524/52 |
| 5,536,264 | 7/1996 | Hsueh | 604/368 |
| 5,562,646 | 10/1996 | Goldman | 604/368 |

FOREIGN PATENT DOCUMENTS

| | | | |
|---|---|---|---|
| A-0210756 | 2/1987 | European Pat. Off. | A61L 15/00 |
| 57-045057-A | 3/1982 | Japan | A41B 13/02 |

*Primary Examiner*—Paul R. Michl
*Attorney, Agent, or Firm*—Carl J. Roof; E. Kelly Linman; Jacobus C. Rasser

[57] ABSTRACT

The present invention provides a superabsorbent material which comprises a combination of (1) an anionic superabsorbent in which from 20 to 100% of the functional groups are in free acid form, and (2) an anion exchanger in which from 20 to 100% of the functional groups are in basic form. The combination is particularly effective as a superabsorbent in the case of electrolyte containing solutions such as menses and urine.

13 Claims, No Drawings

ABSORBENT MATERIAL

The present invention relates to an absorbent material, more particularly a material of the type commonly referred to as a "superabsorbent".

The substances currently termed "superabsorbents" are typically slightly cross-linked hydrophillic polymers. The polymers may differ in their chemical nature but they share the property of being capable of absorbing and retaining even under moderate pressure amounts of aqueous fluids equivalent to many times their own weight. For example superabsorbents can typically absorb up to 100 times their own weight or even more of distilled water.

Superabsorbents have been suggested for use in many different industrial applications where advantage can be taken of their water absorbing and/or retaining properties and examples include agriculture, the building industry, the production of alkaline batteries and filters. However the primary field of application for superabsorbents is in the production of hygienic and/or sanitary products such as disposable sanitary napkins and disposable diapers either for children or for incontinent adults. In such hygienic and/or sanitary products, superabsorbents are used, generally in combination with cellulose fibres, to absorb body fluids such as menses or urine. However, the absorbent capacity of superabsorbents for body fluids is dramatically lower than for deionised water. It is generally believed that this effect results from the electrolyte content of body fluids and the effect is often referred to as "salt poisoning".

The water absorption and water retention characteristics of superabsorbents are due to the presence in the polymer structure of ionisable functional groups. These groups are usually carboxyl groups, a high proportion of which are in the salt form when the polymer is dry but which undergo dissociation and salvation upon contact with water. In the dissociated state, the polymer chain will have a series of functional groups attached to it which groups have the same electric charge and thus repel one another. This leads to expansion of the polymer structure which, in turn, permits further absorption of water molecules although this expansion is subject to the constraints provided by the cross-links in the polymer structure which must be sufficient to prevent dissolution of the polymer. It is assumed that the presence of a significant concentration of electrolytes in the water interferes with dissociation of the functional groups and leads to the "salt poisoning" effect.

Attempts have been made to counteract the salt poisoning effect and improve the performance of superabsorbents in absorbing electrolyte containing liquids such as menses and urine. Thus Japanese Patent Application OPI No. 57-45, 057 discloses an absorbent which comprises a mixture of a superabsorbent such as a cross-linked polyacrylate with an ion exchange resin in powder or granular form. EP-A-0210756 relates to an absorbent structure comprising a superabsorbent and an anion exchanger, optionally together with a cation exchanger, wherein both ion exchangers are in fibrous form. Combining a superabsorbent with an ion exchanger attempts to alleviate the salt poisoning effect by using the ion exchanger, generally as a combination of both an anion exchanger and a cation exchanger, to reduce the salt content of the liquid. The ion exchanger has no direct effect on the performance of the superabsorbent and it may not be possible to reduce the salt content sufficiently to have the desired effect on the overall absorption capacity of the combination. In addition, besides being expensive, the ion exchanger has no absorbing effect itself and thus acts as a diluent to the superabsorbent.

An object of the present invention is to provide a superabsorbent with improved performance in the presence of electrolyte, for example in the case of menses or urine.

The present invention provides a superabsorbent material which comprises a combination of
(1) an anionic superabsorbent in which from 20 to 100% of the functional groups are in free acid form; and
(2) an anion exchanger in which from 20 to 100% of the functional groups are in basic form.

The anionic superabsorbent preferably has from 50 to 100% and more preferably has substantially 100% of the functional groups in free acid form. The cationic superabsorbent preferably has from 50 to 100% and more preferably has substantially 100% in basic form.

As already noted above, anionic superabsorbents have to have functional groups in salt form before they act as superabsorbents. Commercially available superabsorbents are usually available in salt form. It has now surprisingly been found according to the present invention that a combination of an anionic superabsorbent in free acid form with an anion exchanger in basic form is particularly effective as a superabsorbent in the case of electrolyte containing solutions, for example menses and urine.

Whilst not wishing to be bound by any particular theory, it is believed that there is a two fold effect when the superabsorbent material according to the invention is contacted with an electrolyte containing solution as follows:
(1) the anionic superabsorbent is converted from a non-absorbing form into the salt forms in which it acts as a superabsorbent; and
(2) conversion of the anionic superabsorbent into the salt form has a de-ionising effect on the solution which is enhanced by the anion exchanger.

In general the anionic superabsorbent does not behave as an ion exchanger in the sense that contacting the material in acid form with an electrolyte containing solution does not result in conversion to the salt form. The functional groups in anionic superabsorbents are typically carboxyl groups which act as a weak acid which does not dissociate when placed, for example, in a sodium chloride solution. However, presence of the anion exchanger has the effect of attaching chloride ions from sodium chloride solution, thereby displacing the equilibrium in favour of conversion of the anionic superabsorbent into the salt form.

This conversion of the anionic superabsorbent into the salt form on contact with an electrolyte containing solution and the effect of the anion exchanger in attaching chloride ions has a significant desalting effect on the solution thereby improving the performance of the superabsorbent by alleviating the salt-poisoning effect. In contrast with the use of an ion-exchange resin to desalt the solution in combination with a superabsorbent which is already in salt form (see Japanese Patent Application OPI No. 57-45057 and EP-A-0210756 referred to above), the superabsorbent in acid form also has a de-salting effect on the solution. This allows a much greater de-salting effect to be achieved than by use of ion exchanger and superabsorbent in salt form. It should be noted that the effect of the electrolyte in solution on the absorbtion capacity of a superabsorbent for that solution is not linear in that absorption capacity does not decrease regularly with increasing salt content. Accordingly over certain concentration ranges it is possible to bring about a relatively large increase in absorption capacity by effecting a relatively small reduction in salt content of the solution.

The anionic superabsorbent can be any material having superabsorbent properties in which the functional groups are anionic, namely sulphonic groups, sulphate groups, phosphate groups or carboxyl groups. Preferably the functional groups are carboxyl groups. Generally the functional groups are attached to a slightly cross-linked acrylic base polymer. For example, the base polymer may be a polyacrylamide, polyvinyl alcohol, ethylene maleic anhydride copolymer, polyvinylether, polyvinyl sulphonic acid, polyacrylic acid, polyvinylpyrrolidone and polyvinylmorpholine. Copolymers of these monomers can also be used. Starch and cellulose based polymers can also be used including hydroxypropyl cellulose, carboxymethyl cellulose and acrylic grafted starches. Particular base polymers include cross-linked polyacrylates, hydrolysed acrylonitrile grafted starch, starch polyacrylates, and isobutylene maleic anhydride copolymers, Particularly preferred base polymers are starch polyacrylates and cross-linked polyacrylates.

The functional groups will generally be carboxyl groups.

For cellulose derivatives the degree of substitution (DS) of the derivative with the functional group is defined as the number of functional groups (generally carboxyl groups) per anhydroglucose units of cellulose. The DS is generally from 0.1 to 1.5. In an analogous manner the DS for synthetic polymers may be defined as the number of functional groups per monomer or comonomer unit. The DS is generally 1, for example 1 carboxyl group per monomer unit of polyacrylate.

Many anionic superabsorbents are available commercially, for example Favor 922 (Stockhausen), Sanwet IM 1500 (Sanyo), AQU D3236 (Aqualon Company (Hercules)) or DOW 2090. (DOW). A particularly preferred anionic superabsorbent is FAVOR 922 (Stockhausen). Commercially available anionic superabsorbents are generally sold in salt form and need to be converted to the free acid form for use according to the invention, for example by the following method:

Preparation of Favor H 10 g of Favor 922 were placed in a 1 litre beaker, and swelled with 500 ml of distilled water, under continuous stirring with a magnetic stirrer and a magnetic bar. 250 ml of HCl 0.01M were added under continuous stirring, and after 30 minutes the gel was filtered with a nonwoven fabric filter. The acidification and filtration steps were repeated until there were no further sodium ions in the washing waters (the sodium ion content may be determined by a potentometric method using a selective sodium sensitive electrode). Finally the gel was washed with distilled water to remove the excess acid and the gel was dried in an air ventilated oven at 60° C. for 10 hours. The dried polymer obtained was called Favor H.

Ion exchange is the reversible interchange of ions between a solid and liquid in which there is no permanent change in the structure of the solid, which is the ion-exchange material.

Ion exchange occurs in a variety of substances - e.g. silicates, phosphates, fluorides, humus, cellulose, wool, proteins, alumina, resins, lignin, cells, glass, barium sulphate, and silver chloride.

However, they are used for ion exchange materials that depend on properties other than the interchange of ions between liquid and solid phases. Ion exchange has been used on an industrial basis since 1910 with the introduction of water softening using natural and, later, synthetic zeolites.

The introduction of synthetic organic ion exchange resins in 1935 resulted from the synthesis of phenolic condensation products containing either sulfonic or amine groups which could be used for the reversible exchange of cations or anions.

Inorganic ion exchange materials include both the naturally occurring materials such as the mineral zeolites (e.g. cliptonite) the green sands and clay (e.g. the montmorillonite group), and synthetic products such as the gel zeolites, the hydrous oxides of polyvalent metals and the insoluble salts of polybaric acids with polyvalent metals.

Synthetic organic products include cation and anion ion exchange resins both of strong and weak type.

The ability of the weak base resins to sorb acids depends on their own basicity and the pH of the acid involved.

A variety of base strengths are obtained depending on the nature of the amine functionality. Primary, secondary and tertiary amine functionality, or mixtures of them, can be put into various structures ranging from epichlorohydrin amine condensates and acrylic polymers, to styrene-devinyl benzene (DVB) copolymers.

These resins are capable of sorbing strong acids in good capacity but are limited by kinetics.

Strong base, anion exchange resins especially those based on styrene-DVB copolymer are classed as type I and II. Type I is a quaternarized amine product made by the reaction of trimethylamine with the copolymer after chloromethylation with chloromethyl methyl ether (CMME).

The type I functional group is the most strongly basic functional group available and has the greatest affinity for the weak acids that commonly are removing during a water demineralization process (e.g. silic acid and carbonic acid).

Type II functionality is obtained by the reaction of the styrene-DVB copolymer with dimethylethanolamine. This quaternary amine has lower basicity than that of the type I resin, yet it is enough to remove the weak acid anions for most applications.

Quaternary amine functionality has been introduced into pyridinic and acrylate polymers with limited commercial application.

The anion exchanger is preferably an anion exchange resin containing functional groups in basic form. Suitable functional groups include amine groups, i.e. primary, secondary and tertiary amine groups and quaternary ammonium groups. Anion exchange resins which are commercially available and may be used in the present invention are:

Amberlite IRA 400—This is a strong anion exchanger having quaternary ammonium functionality which is available in the chloride form. For use in the present invention it is necessary to convert it to OH⁻form, for example by NaOH treatment in a chromatographic column and washing with distilled water. The total exchange capacity is 3.8 meq/g of dry resin.

Amberlite IRA 68—This a weak basic anion exchanger having tertiary amine functionality which is available in the free base form. The total exchange capacity is 5.6 meq (milliequivalents/g of dry resin). Amberlite ion exchangers are a trade mark of Rohn.

ION exchanger type III from Merck—This is a strong anion exchanger resin, the exchange capacity is about 5 meq/g.

ION exchanger type II form Merck—This is a weak anion exchange resin, the exchange capacity is about 5 meq/g.

Preferred anion exchange resins include Duolite A-102-OH, (Dia-prosim, France) which is a strong anionic exchange resin having quaternary ammonium functionality. The ion exchange capacity is 1.3 meq/ml. Other suitable anion exchange resins can be found in the product ranges of manufacturers such as Rohn and Merck.

In general the weight ratio of anionic superabsorbent to anionic exchanger is in the range 1:20 to 1:1 depending on molecular weight and ion exchange capacity, preferably the weight ratio is 1:2 to 1:4

The absorbent material according to the invention is particularly suitable for use in applications where it is desired to absorb electrolyte containing aqueous liquids. Examples of such liquids include in particular menses and urine and the absorbent material can be used as the filling in catamenials and diapers generally in admixture with a fibrous absorbent such as cellulose fluff. For this purpose the absorbent according to the invention can be present as granules or fibres.

The absorbent materials according to the invention show particularly good absorption of electrolyte containing aqueous liquids as is demonstrated below in the following examples by tests carried out using saline solution (1% NaCl) and synthetic urine.

EXAMPLES

1. Preparation of Favor H+:

10 g of Favor 922 were placed in a 1 litre beaker, and swelled with 500 ml of distilled water, under continuous stirring with a magnetic stirrer and a magnetic bar. 250 ml of HCl 0.01M were added under continuous stirring, and after 30 minutes the gel was filtered with a nonwoven fabric filter. The acidification and filtration steps were repeated until there were no further sodium ions in the washing waters (the sodium ion content may be determined by a potentiometric method using a selective sodium sensitive electrode). Finally the gel was washed with distilled water to remove the excess acid and the gel was dried in an air ventilated oven at 60° C. for 10 hours. The dried polymer obtained was called Favor H.

2. Comparative tests of Liquid Absorption

The test was performed to show that, when in contact with an aqueous saline solution, an anion exchange resin in basic form together with an anionic superabsorbent in acid form act as an anion and cationic exchange mixture and thus deionization of the saline solution occurs. The anionic superabsorbent is then converted to the salt form and thus has improved absorbency due to the low salt content of the solution.

1% NaCl solution (150 ml) was placed in contact with the anion exchange resin A102 OH (3.9 g), in a 250 ml beaker for 2 hours under continuous stirring. This step allows the chloride ions from the solution to be replaced by the hydroxide ions from the resin. The solution was then drawn up by a Pasteur pipette and transferred into another 250 l beaker containing 0.25 g of Favor H being stirred. The addition of solution was stopped when the gel did not well any further. Thereafter the gel was placed into a nonwoven tissue tea bag type envelope, which had one edge which was not sealed, and the absorbency after centrifugation at 60×g for 10 minutes was measured as follows:

$$A=(Wwet-Wdry)/G$$

where:

A=absorbency after centrifugation in g/g

Wwet=weight of envelope containing the wet AGM after centrifugation in g

Wdry=weight of the envelope containing the dry AGM in g

G=weight of the AGM used in the test in g.

Results are as follows:

|  | Amount (g) | Water Retention g/g | |
|---|---|---|---|
|  |  | Deionised Water | 1% NaCl Solution |
| (A) FAVOR (H+) | 0.25 | 30 | 3 |
| (B) FAVOR (Na+) | 0.25 | 400 | 40 |
| (C) ANION EXCHANGE RESIN (A-102-OH) | 3.9 | — | 0.29 |
| (D) FAVOR (H+) + A-102-OH | 0.25 + 3.9 | — | 100 |

NOTE: Results relate to 25 ml of 1% NaCl solution.

The above results show that the anionic superabsorbent in acid form (FAVOR H+) shows very little absorption by itself in 1% NaCl solution. FAVOR Na+ shows some absorbtion but much less than for deionised water. The anion exchange resin has essentially no absorption. However, in combination with the anion exchanger in base form (A-102-OH), FAVOR (H+) shows significantly increased absorption over FAVOR Na+.

It should be noted that 1% NaCl represents a stringent test of the superabsorbent. Studies in the literature show that the salt content of urine varies depending on a number of factors but 1% by weight represents the maximum likely to the encountered in practice.

We claim:

1. A superabsorbent material which comprises a combination of:
   i) an anionic superabsorbent polymer in which from 20 to 100% of the functional groups of the polymer are in free acid form; and
   ii) an anion exchange resin in which from 20 to 100% of the functional groups of the resin are in basic form;
   wherein the superabsorbent material has improved absorbent performance in the presence of polyelectrolyte, relative to the anionic superabsorbent polymer alone.

2. A superabsorbent material as claimed in claim 1 wherein the anionic superabsorbent has from 50 to 100% of the functional groups in free acid form and the anion exchanger has from 50 to 100% and preferably has substantially 100% of the functional groups in basic form.

3. A superabsorbent material as claimed in claim 1 wherein the functional groups in the anionic superabsorbent are sulphonic, sulphate, phosphate or carboxyl groups.

4. A superabsorbent material as claimed in claim 3 wherein the functional groups are carboxyl groups.

5. A superabsorbent material as claimed in claim 1 wherein the functional groups are attached to a polyacrylamide, polyvinyl alcohol, ethylene maleic anhydride copolymer, polyvinylether, polyvinyl sulphonic acid, polyacrylic acid, polyvinylpyrrolidone or polyvinylmorpholine base polymer or copolymer thereof of a starch or cellulose based polymer.

6. A superabsorbent material as claimed in claim 5 wherein the starch or cellulose based polymer is hydroxypropyl cellulose, carboxymethyl cellulose or acrylic grafted starch.

7. A superabsorbent material as claimed in claim 6 wherein the base polymer is a crosslinked polyacrylate, hydrolysed acrylonitrile grafted starch, a starch polyacrylate or a isobutylene maleic anhydride copolymer.

8. A superabsorbent material as claimed in claim 7 wherein the base polymer is a starch polyacrylate or a crosslinked polyacrylate.

9. A superabsorbent as claimed in claim 1 wherein the functional groups in the anion exchange resin are primary, secondary and tertiary amine groups or quaternary ammonium groups.

10. A superabsorbent as claimed in claim 1 wherein the weight ratio of anionic superabsorbent to anionic exchanger is in the range 1:20 to 1:1.

11. A method of using the superabsorbent of claim 1 for the absorption of electrolyte containing aqueous liquids, the method comprising the step of contacting the superabsorbent with the liquid to be absorbed.

12. The method of claim 11 wherein the liquids to be absorbed are menses or urine.

13. A superabsorbent polymer material as claimed in claim 2 wherein the anionic superabsorbent has substantially 100% of the functional groups in free acid form.

* * * * *

UNITED STATES PATENT AND TRADEMARK OFFICE
CERTIFICATE OF CORRECTION

PATENT NO. : 5,804,605
DATED : September 8, 1998
INVENTOR(S) : Palumbo

It is certified that error appears in the above-identified patent and that said Letters Patent is hereby corrected as shown below:

Title page,
Item [30], Foreign Application Priority Data, please delete "TO94A0889" and insert therefor -- TO94A000889 --.
Item [57], ABSTRACT, please delete the entire paragraph and insert therefor -- A superabsorbent material which comprises a combination of an anionic superabsorbent polymer in which from 20 to 100% of the functional groups of the polymer are in free acid form and an anion exchange resin in which from 20 to 100% of the functional groups of the resins are in basic form. --.

Column 1,
Line 7, please delete "hydrophillic" and insert therefor -- hydrophilic --.
Line 35, please delete "salvation" and insert therefor -- solvation --.

Column 5,
Line 20, please delete "H+" and insert therefor -- $H^+$ --.

Column 6,
Line 10, please delete "0.25 +" and insert therefor -- 0.25 --.
Line 11, please delete "3.9" and insert therefor -- +3.9 --.
Lines 41-42, please delete "and preferably has substan-tially 100%".

Column 8,
Line 3, please delete "polymer".

Signed and Sealed this

Twentieth Day of July, 2004

JON W. DUDAS
*Acting Director of the United States Patent and Trademark Office*